(12) United States Patent
Hagelganz et al.

(10) Patent No.: US 7,780,443 B2
(45) Date of Patent: *Aug. 24, 2010

(54) SELF-LIGATING BRACKET WITH ROTARY COVER

(75) Inventors: Rolf Hagelganz, Dundee, OR (US); James TenBrook, Millville, NJ (US)

(73) Assignee: World Class Technology Corporation, McMinnville, OR (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/788,840

(22) Filed: Apr. 20, 2007

(65) Prior Publication Data
US 2007/0259304 A1    Nov. 8, 2007

Related U.S. Application Data

(63) Continuation-in-part of application No. 11/417,685, filed on May 4, 2006, now Pat. No. 7,585,171.

(51) Int. Cl.
*A61C 19/00*    (2006.01)
(52) U.S. Cl. .......................................................... 433/11
(58) Field of Classification Search ................ 433/8–17
See application file for complete search history.

(56) References Cited

U.S. PATENT DOCUMENTS 2,011,575 A    8/1935   Ford (Continued)

FOREIGN PATENT DOCUMENTS

CA    2304243    5/1998

(Continued)

OTHER PUBLICATIONS

Prosecution History for parent U.S. Appl. No. 11/417,685 (all Office Actions and Responses thereto as of Jun. 17, 2009)—Part 1 of 4 Part 1 includes: Resp. to Apr. 1, 2009 Examiner Interview and Mar. 13, 2009 OA, pp. 1-18; Apr. 6, 2009 Examiner's Interview Summary, pp. 19-22; OA Mar. 13, 2009, pp. 24-26.

(Continued)

*Primary Examiner*—Cris L Rodriguez
*Assistant Examiner*—Heidi M Eide
(74) *Attorney, Agent, or Firm*—Chernoff, Vilhauer, McClung & Stenzel LLP (57) ABSTRACT

The present invention provides designs for a self-ligating orthodontic bracket. According to one embodiment, the self-ligating orthodontic bracket includes a mounting base for attachment to a tooth surface, an archwire slot formed upon the base and sized for receiving an orthodontic archwire, a rotary ligating cover selectively rotatable between an open position permitting access to the archwire slot and a closed position covering the archwire slot, and one or more locking features for holding the rotary cover in a closed position. In one embodiment, the bracket includes one or more locking tabs on the rotary cover aligned in coplanar relation to the rotary cover and cooperatively mating with cutout portions in the base. The bracket may include cutouts on the sides of the rotary cover for easier manipulation of the cover. Lead in chamfers on the archwire slot may also be incorporated into the bracket base. Recessed channels and detents may be included for allowing the cover to be held in open or closed positions.

17 Claims, 9 Drawing Sheets

U.S. PATENT DOCUMENTS

| | | |
|---|---|---|
| 2,549,528 A | 4/1951 | Russell |
| 3,578,744 A | 5/1971 | Wildman |
| 4,077,126 A | 3/1978 | Pletcher |
| 4,103,423 A | 8/1978 | Kessel |
| 4,268,249 A | 5/1981 | Forster |
| 4,371,337 A | 2/1983 | Pletcher |
| 4,419,078 A | 12/1983 | Pletcher |
| 4,559,012 A | 12/1985 | Pletcher |
| 4,634,662 A | 1/1987 | Rosenberg |
| 4,655,708 A | 4/1987 | Fujita |
| 4,698,017 A | 10/1987 | Hanson |
| 4,712,999 A | 12/1987 | Rosenberg |
| 4,838,787 A | 6/1989 | Lerner |
| 4,941,825 A | 7/1990 | Lerner |
| 5,037,297 A | 8/1991 | Lerner |
| 5,094,614 A | 3/1992 | Wildman |
| 5,123,838 A | 6/1992 | Cannon |
| 5,248,257 A | 9/1993 | Cannon |
| 5,275,557 A | 1/1994 | Damon |
| 5,299,934 A | 4/1994 | Suyama |
| 5,322,435 A | 6/1994 | Pletcher |
| 5,429,500 A | 7/1995 | Damon |
| 5,466,151 A | 11/1995 | Damon |
| 5,474,445 A | 12/1995 | Voudouris |
| 5,474,446 A | 12/1995 | Wildman et al. |
| 5,613,850 A | 3/1997 | Wildman et al. |
| 5,630,715 A | 5/1997 | Voudouris |
| 5,685,711 A | 11/1997 | Hanson |
| 5,782,631 A | 7/1998 | Kesling et al. |
| 5,863,199 A | 1/1999 | Wildman |
| 6,042,373 A | 3/2000 | Hermann |
| 6,071,118 A | 6/2000 | Damon |
| 6,071,119 A | 6/2000 | Christoff et al. |
| 6,168,428 B1 | 1/2001 | Voudouris |
| 6,190,166 B1 | 2/2001 | Sasakura |
| 6,193,508 B1 | 2/2001 | Georgakis |
| 6,247,923 B1 | 6/2001 | Vahsi |
| 6,347,939 B2 | 2/2002 | Abels |
| 6,394,798 B1 | 5/2002 | Huff |
| 6,554,612 B2 | 4/2003 | Georgakis et al. |
| 6,632,088 B2 | 10/2003 | Voudouris |
| 6,726,474 B2 | 4/2004 | Spencer |
| 6,776,613 B2 | 8/2004 | Orikasa |
| 6,866,505 B2 | 3/2005 | Senini |
| 7,063,529 B2 | 6/2006 | Abels et al. |
| 2004/0072117 A1 | 4/2004 | Farzin-Nia et al. |
| 2004/0157186 A1 | 8/2004 | Abels et al. |
| 2004/0166458 A1 | 8/2004 | Opin et al. |
| 2005/0186525 A1 | 8/2005 | Abels et al. |
| 2005/0239012 A1 | 10/2005 | Bathen et al. |
| 2005/0244773 A1 | 11/2005 | Abels et al. |
| 2005/0244774 A1 | 11/2005 | Abels et al. |
| 2005/0255422 A1 | 11/2005 | Cordato |
| 2006/0003281 A1 | 1/2006 | Nicholson |
| 2006/0003282 A1 | 1/2006 | Nicholson |
| 2006/0024634 A1 | 2/2006 | Lai et al. |
| 2006/0024635 A1 | 2/2006 | Lai |
| 2006/0051721 A1 | 3/2006 | Carriere Lluch |
| 2006/0084025 A1 | 4/2006 | Abels et al. |
| 2006/0110699 A1 | 5/2006 | Forster |
| 2006/0147868 A1 | 7/2006 | Lai et al. |
| 2006/0154196 A1 | 7/2006 | Oda |

FOREIGN PATENT DOCUMENTS

| | | |
|---|---|---|
| MX | PA/A/2000/0008056 | 12/2001 |
| WO | WO 99/40871 | 8/1999 |
| WO | WO 2004/047665 A1 | 6/2004 |

OTHER PUBLICATIONS

Prosecution History for parent U.S. Appl. No. 11/417,685 (all Office Actions and Responses thereto as of Jun. 17, 2009)—Part 2 of 4 Part 2 includes: Resp. to Jan. 28, 2009 OA, pp. 1-13; OA Jan. 28, 2009 pp. 14-18; Resp. to Nov. 5, 2008 OA pp. 19-21; OA Nov. 5, 2008 pp. 22-31; Resp. to Jul. 28, 2008 OA, pp. 32-40.

Prosecution History for parent U.S. Appl. No. 11/417,685 (all Office Actions and Responses thereto as of Jun. 17, 2009)—Part 3 of 4 Part 3 includes: Supp. OA Jul. 28, 2008, pp. 1-19; OA Apr. 21, 2008 pp. 20-40.

Prosecution History for parent U.S. Appl. No. 11/417,685 (all Office Actions and Responses thereto as of Jun. 17, 2009)—Part 4 of 4 Part 4 includes: Response to Nov. 6, 2007 OA, pp. 1-13; OA Nov. 6, 2007, pp. 14-33.

SELF-LIGATING BRACKET WITH ROTARY COVER

CROSS-REFERENCE TO RELATED APPLICATIONS

This application is a continuation-in-part of U.S. patent application Ser. No. 11/417,685, filed May 4, 2006, now issued on Sep. 8, 2009, as U.S. Pat. No. 7,585,171, which has the title "Orthodontic Bracket with Rotary Ligating Cover," the specification of which is incorporated herein by reference.

BACKGROUND OF THE INVENTION

This disclosure relates to self-locking or ligatureless orthodontic brackets. More particularly, this disclosure relates to self-ligating orthodontic brackets each having a rotary ligating cover for retaining an archwire therein.

Orthodontic treatment generally comprises dental work to correct irregularities of the teeth or of the relation of the teeth to surrounding anatomy. The irregularities may involve malocclusions with varying degrees of severity. Class 1 malocclusions, for example, may involve spacing irregularities such as excessive crowding or diastema (a gap between two adjacent teeth). Class 2 malocclusions may involve overbite conditions where the upper anterior teeth project labially over the lower anterior teeth. Class 3 malocclusions, in contrast, may involve underbite conditions where the upper anterior teeth close within the lingual side of the lower anterior teeth. For these and other observed irregularities, treatment typically involves installation of braces or mechanical aids for repositioning the teeth into correct orthodontic alignment.

Braces generally include orthodontic brackets configured for attachment to the labial or lingual surfaces of the teeth or for attachment to metallic bands secured around the teeth. The brackets typically include archwire slots within which a flexible yet resilient archwire may be engaged. Each bracket is typically bonded to the tooth surface so that the bracket's archwire slot is oriented for engagement with the archwire. Various techniques are used for orienting the brackets. For example, an edgewise appliance comprises braces whereby each bracket is oriented and bonded to the tooth so that the archwire slot is perpendicular to the long axis of the root of the tooth. Alternatively, a straight-wire appliance includes braces whereby each bracket is oriented and bonded to the tooth so that the archwire slot is parallel to the occlusal plane (the plane of the biting surfaces of the teeth).

The archwire is typically a curved metallic wire having a rectangular or circular cross section that is bent or twisted prior to engagement with the brackets. The memory or restoring force exerted by the archwire upon the brackets serves to move the teeth into the desired alignment. Throughout the duration of orthodontic treatment, the orthodontist periodically adjusts the shape of the archwire (as well as the configuration of other attachments such as elastic bands and so forth) to achieve the correct orthodontic alignment.

Most brackets in current use incorporate tie wings or extensions that project upwardly and downwardly in a gingival-occlusal orientation and require the use of ligatures or ligating modules to hold the archwire within the archwire slots. The ligatures or ligating modules are typically donut-shaped elastomeric rings or wires that are stretched around or twisted around the tie wings.

The use of such ligatures or ligating modules presents a number of inherent disadvantages, some of which are mentioned herein. The small size of the ligatures or ligating modules requires substantial time for installation of the archwire. Because the orthodontist will typically make numerous adjustments to the archwire throughout orthodontic treatment, the orthodontist will likely remove and replace the ligatures or ligating modules numerous times. Hygiene is another problem since the use of ligatures or ligating modules increases the areas where food particles may be trapped. Further, with movement due to chewing or other activities, the ligatures or ligating modules may become detached altogether, allowing the archwire to disengage from the archwire slots.

Ligatures or ligating modules also present other limitations in terms of the forces exerted upon the brackets. For example, the labial or outward force that may be applied to a tooth having a bracket bonded to its labial surface is limited to the strength of the ligature or ligating module in the labial direction. On the same tooth, the force that may be applied in the lingual direction is not so constrained (because the force is applied against the bracket structure rather than the ligature or ligation module).

Traditional bracket systems generally rely on active ligation using elastomeric or wire ligatures wrapped about the tie wings of the bracket to hold the archwire into the archwire slot. The two areas that hold the archwire most securely are the mesial and distal ends of the bracket where the elastomeric or wire ligatures make contact with the archwire, binding the archwire. This binding creates friction during orthodontic tooth movement and consequently increases the forces needed for leveling and sliding tooth movement during treatment.

By contrast, passive self-ligating (or so-called frictionless) bracket systems, or bracket systems that do not require traditional ligatures or ligating modules, have been developed which rely on a principle that forces employed to reposition teeth should not overwhelm the supporting periodontium and facial musculature. Forces applied should instead be minimized to a level just large enough to stimulate cellular activity and, thus, tooth movement without unnecessarily disturbing the vascular supply to the periodontium.

Several self-locking or self-ligating (ligatureless) orthodontic brackets have been designed. However, most of those have complex designs, incorporating features requiring prohibitively expensive machining operations or comprising multiple separate parts, which in turn increases the number of failure modes for such brackets. Other designs have been rejected in the marketplace due to poor quality or poor design, a lack of available features, difficulty of use, or other factors.

What is needed, therefore, is an orthodontic bracket that incorporates a self-ligating capability and that offers a different style of bracket than those available today.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

For a more complete understanding of the present invention, the drawings herein illustrate examples of the invention. The drawings, however, do not limit the scope of the invention. Similar references in the drawings indicate similar elements.

DETAILED DESCRIPTION OF PREFERRED EMBODIMENTS

In the following detailed description, numerous specific details are set forth in order to provide a thorough understanding of the present invention. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Various operations will be described as multiple discrete steps performed in turn in a manner that is helpful for understanding the present invention. However, the order of description should not be construed as to imply that these operations are necessarily performed in the order they are presented, nor even order dependent.

Figure 1A:
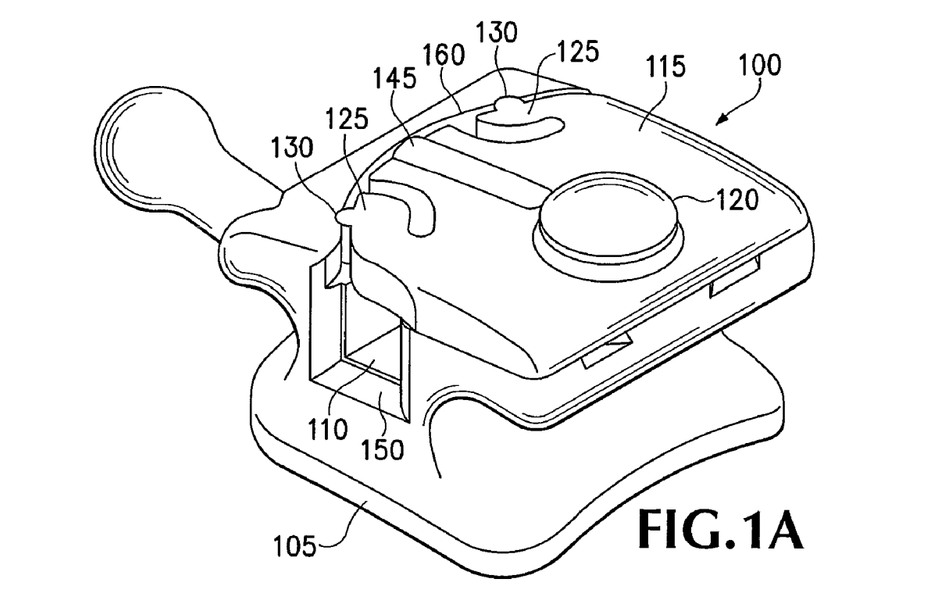
FIGS. 1A and 1B illustrate isometric views of self-ligating orthodontic brackets according to various embodiments of the invention.

Turning now to the several drawings, FIG. 1A illustrates an isometric view of a self-ligating orthodontic bracket 100 according to one embodiment of the invention. The self-ligating orthodontic bracket 100 includes a mounting base 105 for attachment to a tooth surface, an archwire slot 110 formed upon the mounting base 105 and sized for receiving an orthodontic archwire (not shown), and a rotary ligating cover 115 (shown in a closed position) for retaining an orthodontic archwire within the archwire slot 110. As will be discussed in greater detail below, the rotary ligating cover 115, in one embodiment, comprises a plate (as shown) that may rotate about an axial member such as a retaining pin 120 positioned in an eccentric manner, i.e., the pivot point positioned on one side of the bracket 100, and having a pivot axis oriented perpendicular to the archwire slot 110 and substantially normal to the tooth surface and mounting base 105 bonded thereon. The rotary ligating cover 115 preferably includes one or more coplanar resilient retention features (or locking mechanisms) 125 for holding the rotary ligating cover 115 in a closed position thereby retaining an orthodontic archwire within the archwire slot 110.

As shown in FIG. 1A, the one or more coplanar resilient retention features 125 may comprise resilient portions of the rotary ligating cover 115 suitably formed to allow coplanar deflection and subsequent locking of one or more protruding surfaces of the rotary ligating cover 115 with one or more corresponding indentations 130. Here, the resilient retention features 125 have been designed to deflect inward, toward the axis of the retaining pin 120, for lockable engagement between one or more protruding surfaces (or locking tabs) of the rotary ligating cover 115 and one or more cooperatively mating indentations 130. In this configuration, the resilient retention features 125 deflect and engage with the mating indentations 130 in directions coplanar with the rotary ligating cover 115. Consequently, forces exerted normal to the rotary ligating cover 115 (i.e., forces in a labial-lingual direction) as may arise due to movement of an archwire retained within the archwire slot 110, are not likely to affect the retention of the archwire within the archwire slot 110. Thus, the self-ligating orthodontic bracket 100 more securely retains an archwire than other bracket designs.

Also shown in FIG. 1A, the self-ligating orthodontic bracket 100 may include one or more orthodontic tool features such as an outer surface feature 145 of the rotary ligating cover 115. The outer surface feature 145 may be a protruding ridge (as shown), a recessed groove (not shown), a circular recessed area, or any of a number of suitable shapes and configurations that may improve the ease of use of the bracket 100. For instance, an orthodontic tool such as an explorer or scaler may be used with the outer surface feature 145 to rotatably open or close the rotary ligating cover 115 to expose or cover, respectively, the archwire slot 110. Likewise, pliers or another orthodontic tool may be used with the outer surface feature 145 (perhaps along with one side of the bracket 100) to close the rotary ligating cover 115. Further, the outer surface feature 145, alone or in combination with the retaining pin 120 and other visual aspects of the bracket 100, preferably provides a centerline for the bracket 100 useful to aid the orthodontist in the placement of the bracket 100 upon the patient's tooth.

The self-ligating orthodontic bracket 100 preferably includes rounded edges and chamfered archwire slot ends 150 to improve comfort for the patient wearing the orthodontic appliance. As shown and as will be depicted in many of the illustrations herein, the rotary ligating cover 115, the exterior pan head shape of the retaining pin 120, and other features which may define the outer surfaces of the bracket 100 opposite the mounting base 105, preferably comprise smooth and rounded shapes to improve patient comfort and minimize the overall side profile or outward dimension of the bracket 100 from the bonding surface of the mounting base 105. Preferably, the outer surfaces of the one or more indentations 130 and the neighboring edges 160 therebetween are coplanar and flush with the outer surfaces of the rotary ligating cover 115 and, in particular, with the outer surfaces of the one or more resilient retention features 125 and the neighboring or adjacent outer surfaces therebetween.

Figure 1B:
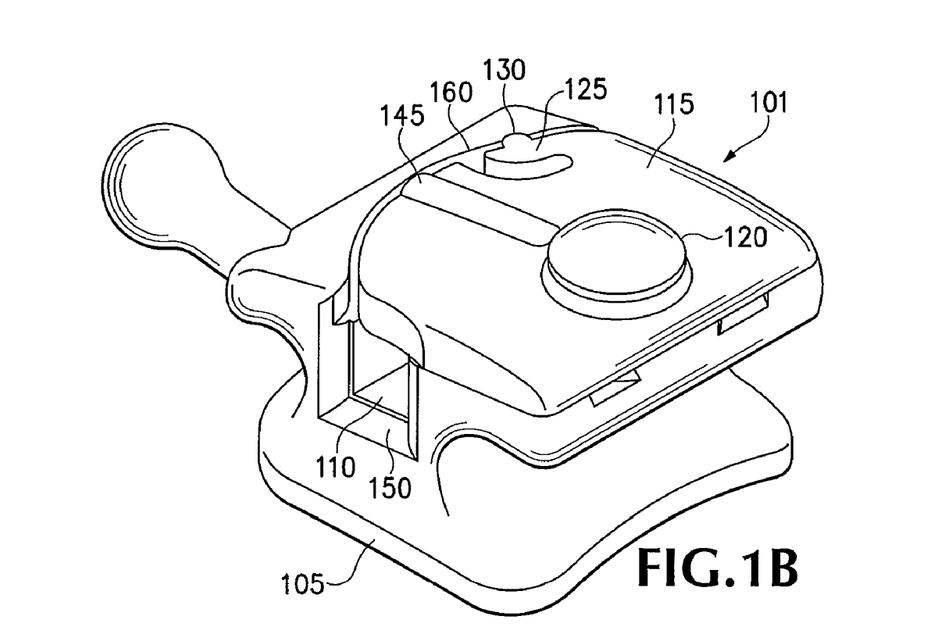

FIG. 1B illustrates an exemplary orthodontic bracket 101 having just one coplanar resilient retention feature (or locking mechanism) 125 with just one corresponding (cooperatively mating) indentation 130.

Figure 2A:
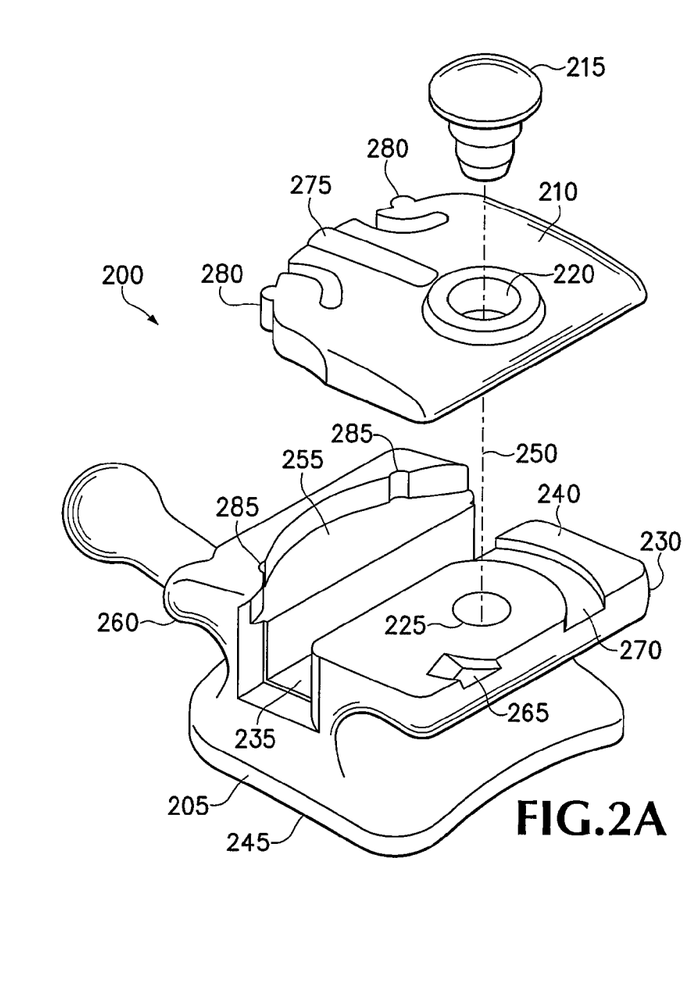
FIGS. 2A and 2B illustrate exploded isometric views of self-ligating orthodontic brackets each having a bracket base, rotary ligating cover, and retaining pin, according to various embodiments of the invention.

FIG. 2A illustrates an exploded isometric view of a self-ligating orthodontic bracket 200 having a bracket base 205, rotary ligating cover 210, and retaining pin 215, according to one embodiment of the invention. As shown, the rotary ligating cover 210 may be rotatably fastened to the bracket base 205 using retaining pin 215 inserted through a hole 220 in the rotating cover 210 and journalled into a corresponding hole 225 in a tie wing 230 formed on one side of the archwire slot 235. The outward surface 240 of the bracket 205, opposite the tooth mounting surface 245 and upon which the rotary ligating cover 210 may be rotated when fastened to the bracket 205, preferably encompasses substantially all of the outward facing surface area of the tie wing 230, and an axis of rotation 250 of the rotary ligating cover 210 extends through the outward surface 240. A coplanar portion 255 of the opposing tie wing 260 on the other side of the archwire slot 235 receives the bottom surface of the rotary ligating cover 210 so that the rotary ligating cover 210, when in a closed position, covers substantially the full length of the archwire slot 235.

As will be described in further detail, the outward surface 240 preferably incorporates one or more concentric circular recesses 265 and 270 for limiting rotation of the rotary ligating cover 210 due to asymmetries of the bracket 200. For example, for brackets 200 having a rhomboid or parallelogram overall shape as viewed from the outward surface of the bracket looking toward the tooth mounting surface 245 (or a frontal view), the rotary ligating cover 210 need not be symmetrical about its centerline, the centerline formed by the through hole 220 and (as shown) the outer surface feature 275. For such an asymmetrical rotary ligating cover 210, one or more circular recess 265 and 270 may be used in combination with engagement of the one or more locking tabs 280 with cooperatively mating cutout portions or indentations 285 to establish a closed position for the rotary ligating cover 210 when the rotary ligating cover 210 is rotated in a clockwise direction about the axis of rotation 250 as viewed from the outward surface of the bracket 200 looking toward the tooth mounting surface 245. As will be shown in successive views, the rotary ligating cover 210 may incorporate a protruding nub on its lower surface that tracks within the concentric circular recesses 265 and 270.

In the embodiment shown in FIG. 2A, the rotary ligating cover 210 may be closed to cover the archwire slot 235 by turning the rotary ligating cover 210 in a clockwise direction until the looking tabs 280 engage with the cooperatively mating indentations 285 formed upon the tie wing 260 and the protruding nub (not shown) reaches the end of (or just beyond the end of) the circular recess 265. The rotary ligating cover 210 may be opened to expose the archwire slot 235 by turning the rotary ligating cover 210 in a counterclockwise direction whereby the protruding nub moves first within the circular recess 265 and then the circular recess 270 until the archwire slot 235 is fully exposed.

Figure 2B:
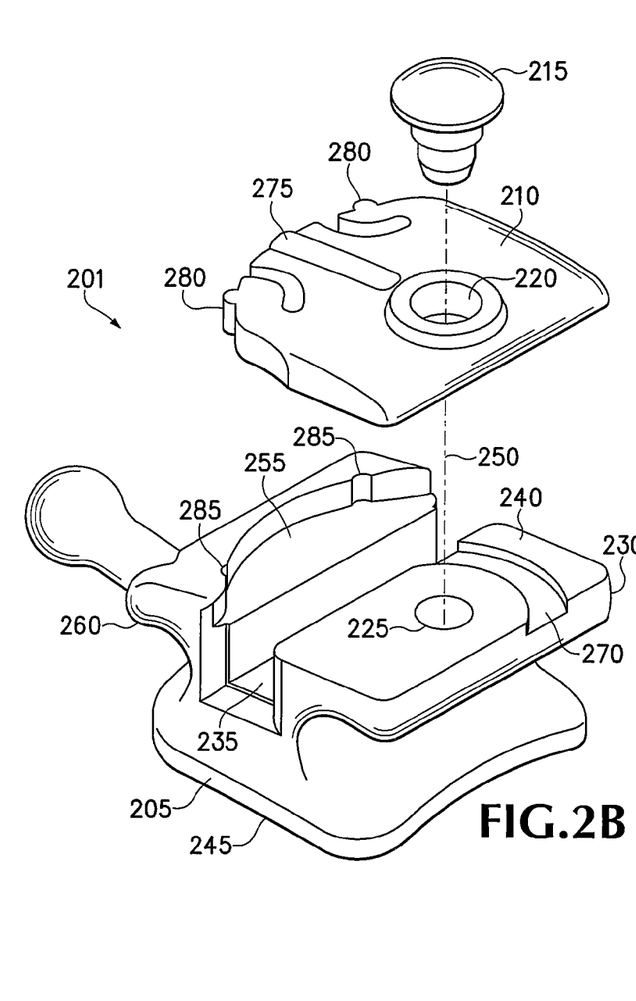

FIG. 2B illustrates an exemplary orthodontic bracket 201 having just one circular recess 270, i.e. without the circular recess 265 as shown in FIG. 2A.

Figure 3:
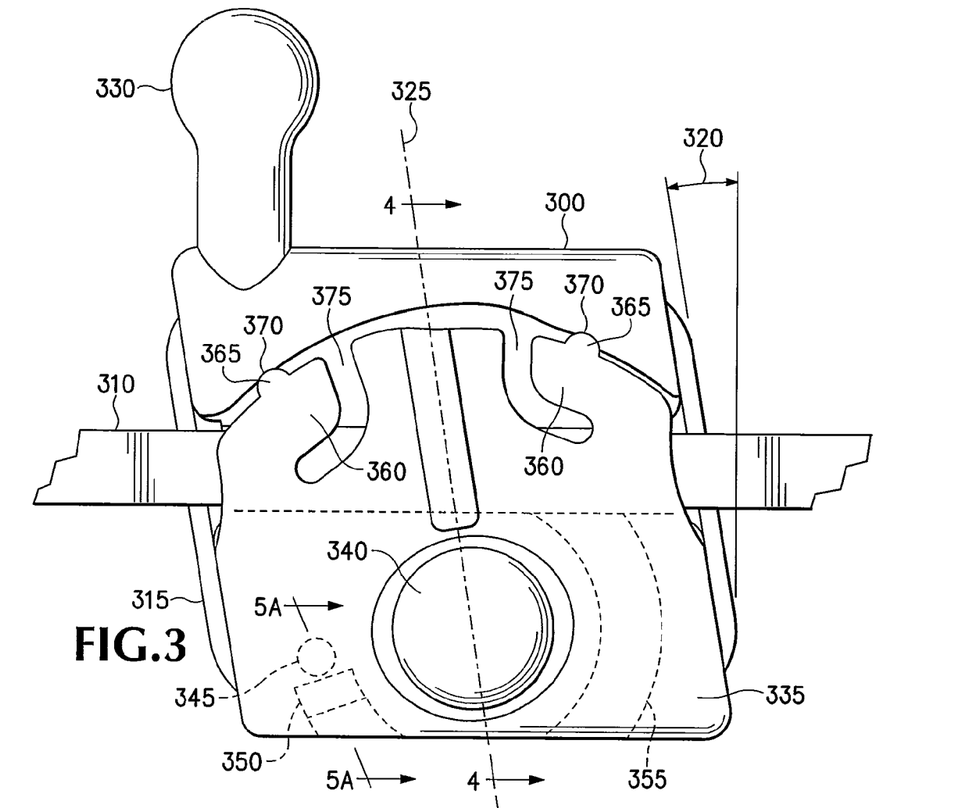
FIG. 3 is an exemplary frontal view of a self-ligating orthodontic bracket engaged with an archwire.

Next, FIG. 3 is an exemplary frontal view of a self-ligating orthodontic bracket 300 engaged with an archwire 310. The bracket 300 may be mounted to the labial (front) surface of a tooth as part of a typical bracket system. Or, alternatively, the bracket 300 may be mounted on the lingual (back) of a tooth surface as part of a lingual or "hidden" bracket system. As will be discussed further, the frontal profile of the bracket 300 may be designed for use on particular tooth surfaces. For example, the bracket 300 may be designed to have a particular rhomboid or parallelogram profile for bonding to a particular tooth, such as one of the upper or lower centrals, laterals, cuspids, bicuspids, molars, and so on.

The archwire 310 may be retained within the self-ligating bracket 300 so that the archwire 310 runs in a mesial-distal orientation, parallel to the occlusal surface (the cutting or incisal edge) of a tooth. Other orientations may be used with the bracket 300. However, this orientation is typical of a straight-wire (or Roth) appliance whereby crown angulation and crown inclination are engineered into the bracket 300 thereby allowing use of an archwire that is "straight" or parallel to the cutting edge of each tooth (when the teeth are positioned in correct orthodontic alignment). Crown angulation is generally the mesial-distal to gingival-occlusal orientation of the tooth and is affected by the mesial-distal orientation of the archwire slot (or slot tip). Crown inclination is generally the labial-lingual to gingival-occlusal orientation of the tooth and is affected by the rotational orientation of the archwire slot (or slot torque) along the mesial-distal (or archwire) axis.

The bracket 300 shown in FIG. 3 has an engineered slot tip 320, which is the angular offset between the centerline 325 of the bracket 300 and a line perpendicular to a mesial-distal line that is parallel with the archwire 310. In orthodontic practice, the bracket 300 may be bonded to a tooth surface so that the centerline 325 of the bracket 300 is aligned with the gingival-occlusal axis (or long axis) of the tooth's clinical crown.

Whereas a straight-wire appliance typically includes individually engineered brackets with each bracket having the desired crown inclination (slot torque) and crown angulation (slot tip) for a particular tooth, other techniques may be used which require different orientations. For example, a standard edgewise appliance typically includes brackets having a rectangular profile and an orientation such that the centerline of the bracket is aligned along the gingival-occlusal axis (or long axis) of the clinical crown and perpendicular with the archwire slot. Typically, the brackets in a standard edgewise appliance have archwire slots that are not parallel to the incisal edges of the teeth (when the teeth are positioned in correct orthodontic alignment). Instead, the archwire is angled, bent, and twisted to define the desired position of the teeth.

As commonly practiced in orthodontic treatment, brackets may be fabricated for a particular patient by prescription. The brackets may be engineered to include the appropriate slot torque and slot tip for each individual tooth for the particular patient. For example, specifically engineered brackets may be fabricated for the upper left central, the upper left lateral, the upper left cuspid, and so forth moving distally toward the upper left molars (using Palmer's notation for designating individual teeth). Each bracket typically incorporates a particular slot torque and slot tip as well as other features as may be needed. For instance, the bracket for the upper left cuspid may include a slot tip 320 of, perhaps, 9° and include a ball hook 330 for use with elastics or other features of the orthodontic appliance.

Still referring to FIG. 3, the mounting base 315 of the bracket 300 may be sized to fit a particular tooth surface. For example, the mounting base 315 may be wider at the incisal end of the tooth to match the shape of the tooth surface. The bracket 300 may be bonded to the surface of a tooth, or, alternatively, to a band assembly which is attached to the tooth. The bracket 300 is oriented so that the rotary ligating cover 335 pivots about an axial member 340 positioned on the tie wing on the side of the archwire slot closest to the incisal end of the tooth surface (and opposite the gingival end).

However, the bracket may be oppositely oriented so that the rotary ligating cover 335 pivots about an axial member 340 positioned on the on the gingival side of the archwire slot.

For the particular bracket 300 shown in FIG. 3, the rotary ligating cover 335 follows the overall rhomboid or parallelogram shape of the bracket 300 and is not symmetrical about its centerline 325. A protruding nub or rotation stop 345 may be formed upon the underside of the rotary ligating cover 335 designed to track within concentric circular recesses 350 and 355 when the rotary ligating cover 335 pivots about the axial member 340. For example, as the rotary ligating cover 335 is rotated in a counterclockwise direction from the closed position shown, the rotation stop 345 slides into and follows the first circular recess 350, and, with further rotation, follows freely within the second circular recess 355. Likewise, as the rotary ligating cover 335 is rotated in a clockwise (or closing) direction, the rotation stop 345 follows freely within the second circular recess 355 and then follows within the first circular recess 350 until sliding up to and slightly beyond the end of the first circular recess 350.

As the rotary ligating cover 335 rotates in a clockwise direction about the axial member 340, the resilient retention features (or mechanisms) 360 deflect inward, toward the axial member 340 until locking tabs 365 engage with cooperatively mating cutout portions (or indentations) 370. In the embodiment shown, the resilient retention features 360 resemble coplanar fingers within the rotary ligating cover 335, whereby relief channels 375 permit flexing of at least portions of the resilient retention features 360 adjacent to the locking tabs 365.

As will be appreciated, in one embodiment the orientation of concentric circular recesses 350 and 355, and associated rotation stop 345, may be reversed such that the rotary ligating cover 335 may be opened in a clockwise direction of rotation and closed in a counterclockwise direction of rotation. Further, the cutout portions such as concentric circular recesses 350 and 355 may be formed upon the rotary ligating cover 335 instead of the bracket base 315, and the rotation stop 345 may be formed upon the bracket base 315 instead of the rotary ligating cover 335. Likewise, the positions of the locking tabs 365 and corresponding indentations 370 may be reversed, according to one embodiment, yet still provide the intended function. The bracket 300 may include one or more locking tabs (such as locking tabs 365) aligned in coplanar relation to the rotary ligating cover 335 and cooperatively mating with cutout portions in the rotary ligating cover. In other words, the one or more locking tabs may be formed upon the bracket base, and the cooperatively mating cutout portions, to which the locking tabs engage when the ligating cover is in a closed position, may be formed upon the rotary ligating cover.

Figure 4:
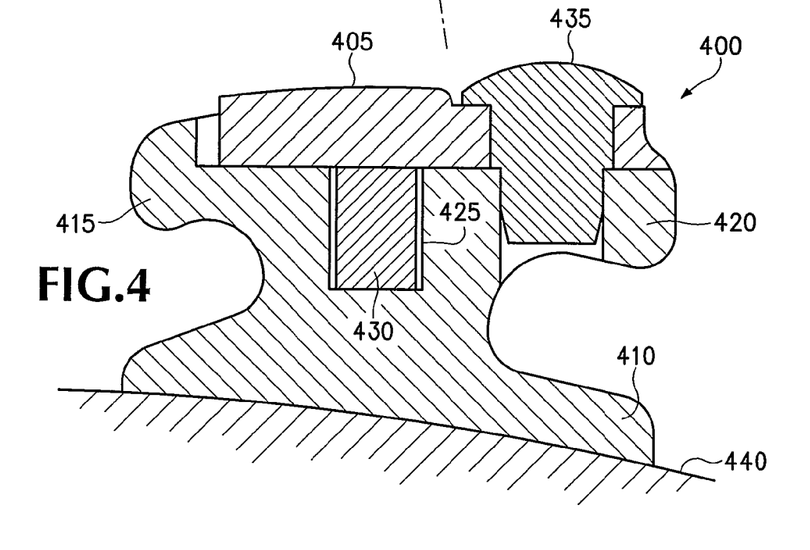
FIG. 4 is a sectional view of a self-ligating orthodontic bracket with a rotary ligating cover in a closed position, according to one embodiment of the invention.

Next, FIG. 4 is a sectional view (such as through centerline 325 in FIG. 3) of a self-ligating orthodontic bracket 400 with a rotary ligating cover 405 in a closed position, according to one embodiment. The bracket 400 includes a mounting base 410 and a pair of tie wings 415 and 420 formed thereon and extending outward, away from the mounting base 410, and defining an archwire slot 425 therebetween. The archwire slot 425 is sized for receiving an orthodontic archwire 430, and the rotary ligating cover 405 is selectively rotatable between a closed position (as shown) for securably retaining the archwire 430 within the archwire slot 425 and an open position (not shown) for permitting access to the archwire slot 420. The rotary ligating cover 405 may rotate about an axial member such as a retaining pin 435 positioned on one side of the bracket 400 such as on one of the tie wings 420. The retaining pin 435 shown incorporates a pan head extending over the outward surface of the rotary ligating cover 405 and a lower portion journalled or fastenably attached into a receiving hole or recess area in the tie wing 420. As shown, the retaining pin 435 may be dimensioned with a smaller diameter that is inserted into the receiving hole in the tie wing 420 and a larger diameter about which the rotary ligating cover 405 may slidably rotate. The smaller diameter, according to one embodiment, permits a press-fit operation for retaining the rotary ligating cover 405 to the bracket 400 whereby the smaller diameter of the retaining pin (or dowel) 435 is forcibly pressed into the receiving hole in the tie wing 420. However, other configurations may be used. For example, a retaining pin having a single diameter may be used, perhaps with precision fastening equipment to ensure that the retaining pin is able to rotate freely about the retaining pin.

The pair of tie wings (as shown, 415 and 420) generally extend transverse to the archwire slot 425 with one tie wing (i.e., 415) extending from the archwire slot 425 in a gingival direction and the other (i.e., 420) extending from the archwire slot 425 in an occlusal direction. The tie wings 415 and 420 provide additional utility and flexibility for the orthodontist in applications where the use of standard elastomeric ligatures or other attachments requiring tie wings may be desired. The use of standard elastomeric ligatures creates friction between the archwire and the elastomeric ligature. The friction, or active engagement, with the archwire 430 allows for additional forces to be applied to a tooth surface 440 bonded to the bracket 400. For example, active engagement with the archwire 430 may be used to urge tooth movement along the mesial-distal (or archwire) axis (to increase or decrease spacing between adjacent teeth). Active engagement with the archwire 430 may also be used to increase the forces applied to change crown angulation (affected by slot tip) and crown inclination (affected by slot torque).

In contrast, the self-ligating bracket 400 may rely on passive engagement with the archwire 430. With passive engagement, the archwire 430 is not forcibly restrained within the archwire slot 425 and is instead allowed to move within the archwire slot 425. Such brackets may comprise a passive or so-called frictionless bracket system and do not require traditional ligatures or ligating modules. In such systems, the archwire 430 is free to slide within the archwire slot 425 along the mesial-distal axis.

As previously discussed, crown inclination is generally the labial-lingual to gingival-occlusal orientation of the tooth and is affected by the rotational orientation of the archwire slot 430 along the mesial-distal axis. An axial (or sectional) view of the bracket 400 along the mesial-distal axis is shown in FIG. 4. Here, the archwire slot 425 is shown angled (or rotated) slightly such that the labial-lingual sides of the archwire slot 425 (which are normal to the rotary ligating cover 405) are not perpendicular (or not normal) to the tooth surface 440. This is a typical rotational orientation for the archwire slot used in a straight-wire appliance where slot torque is engineered into the bracket. A standard edgewise appliance, in contrast, typically includes an archwire slot with sides perpendicular to the mounting surface of the tooth.

Figure 5A:
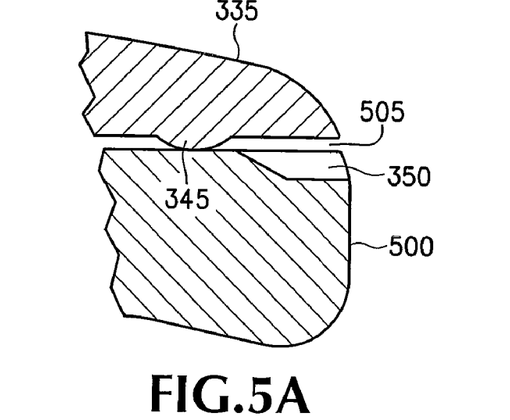
FIGS. 5A-5C are sectional views of a rotary ligating cover upon a bracket base in closed and partially open positions, according to various embodiments of the invention.
Figure 5B:
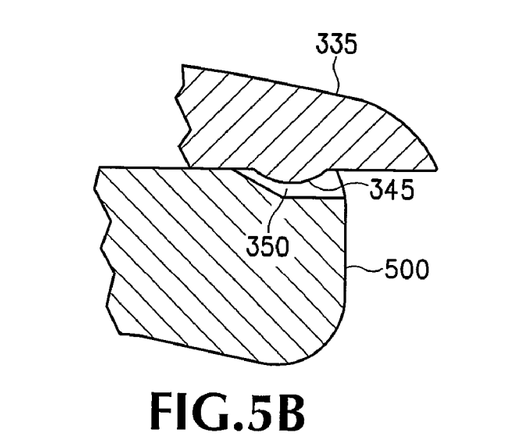
Figure 5C:
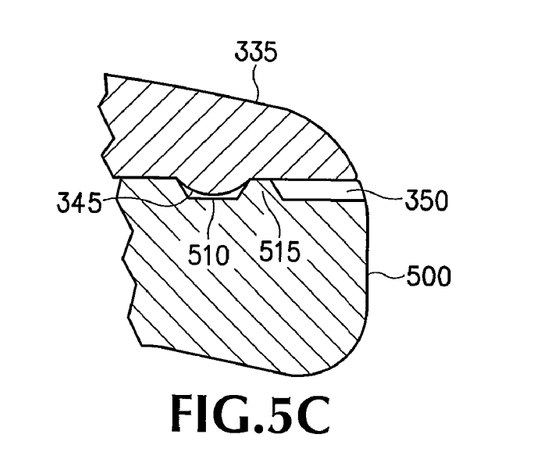

Turning now to FIGS. 5A-5C, sectional views are provided showing the rotary ligating cover 335 upon a bracket base 315 (or a tie wing 500 thereon) in closed and partially open positions, according to various embodiments of the invention. FIG. 5A is the sectional view indicated in FIG. 3 and shows the rotary ligating cover 335 in a closed position with the rotation stop 345 slightly beyond the end of the circular recess 350. The slight separation 505 between the rotary ligating cover 335 and the mating surface of the tie wing 500 may provide additional retention forces for holding the rotary ligating cover 335 in a closed position. For example, the frictional forces between the rotation stop 345 and the outward surface of the tie wing 500 and the frictional forces involving the axial member (not shown) retaining the rotary ligating cover 335 may provide additional retention forces beyond the retention forces provided by engagement of other locking features associated with the rotary ligating cover 335, such as, for example, coplanar locking tabs along the edge surface of the ligating cover 335.

FIG. 5B is a sectional view as in FIG. 5A with the rotary ligating cover 335 in a partially open position with the rotation stop 345 shown tracking within the circular recess 350. Here, the rotary ligating cover 335 has been partially opened (in a counterclockwise direction) whereby the rotation stop 345 has dropped into the circular recess 350.

FIG. 5C is a sectional view as in FIG. 5A, according to one embodiment, showing the rotary ligating cover 335 in a closed position with the rotation stop 345 formed upon the lower surface of the ligating cover 335 and positioned outside of or beyond the end of the circular recess 350. However, the rotation stop 345 in FIG. 5C is shown seated within a cooperatively mating cutout portion or detent 510 of the outward surface of the tie wing 500 and, thereby, holding the rotary ligating cover 335 in a closed position. In operation, as the ligating cover 335 is rotated, the rotation stop 345 may enter the circular recess (or recessed channel) 350, as shown in FIG. 5B, ride over bracket material 515 at the end of the circular recess 350, and seat into the detent 510.

Figure 6A:
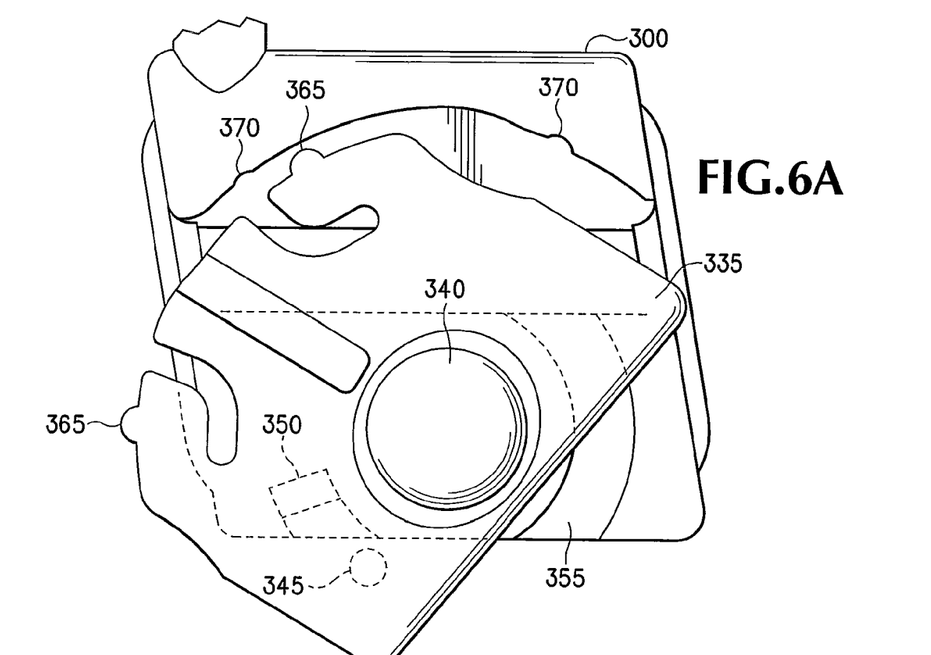
FIGS. 6A and 6B are top views of self-ligating orthodontic brackets each with a rotary ligating cover in a partially open position, according to various embodiments of the invention.

FIG. 6A is a top view of a self-ligating orthodontic bracket with a rotary ligating cover 335 in a partially open position, according to one embodiment of the invention. As the rotary ligating cover 335 is opened (rotating the cover 335 in a counterclockwise direction), the rotation stop 345, in one embodiment, leaves the circular recess 350. Also shown in FIG. 6A are the relative positions of locking tabs 365 and their cooperatively mating cutout portions (or indentations) 370, according to one embodiment. As the rotary ligating cover 335 opens, pivoting about the axial member 340, the locking tabs 365 become unseated from their corresponding indentations 370 allowing the rotary ligating cover 335 to rotate more freely.

Figure 6B:
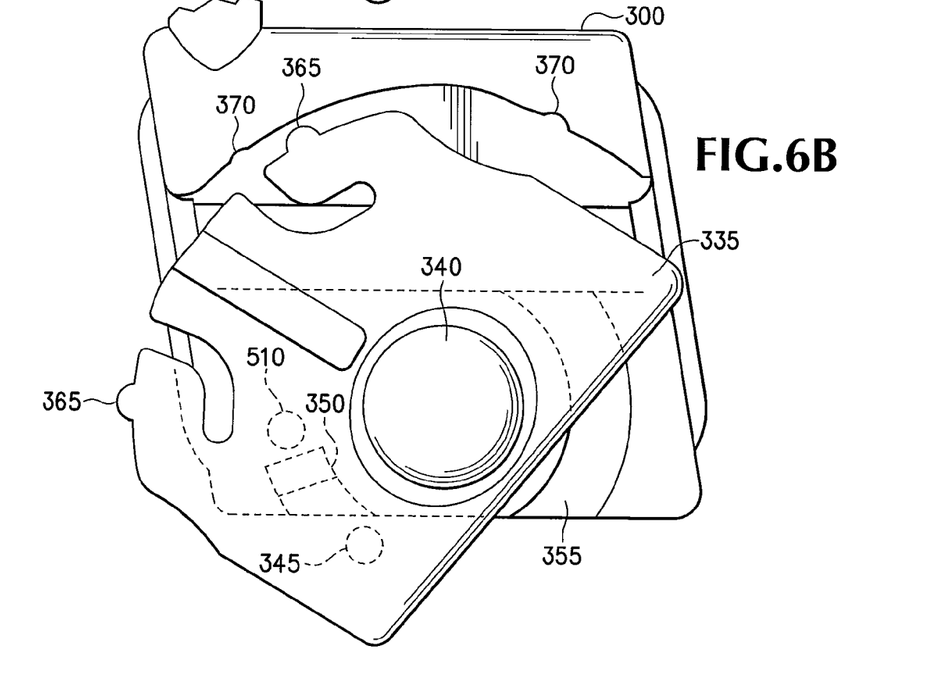

FIG. 6B is a top view of a self-ligating orthodontic bracket incorporating a detent 510 as in sectional view FIG. 5C, according to one embodiment.

Figure 7:
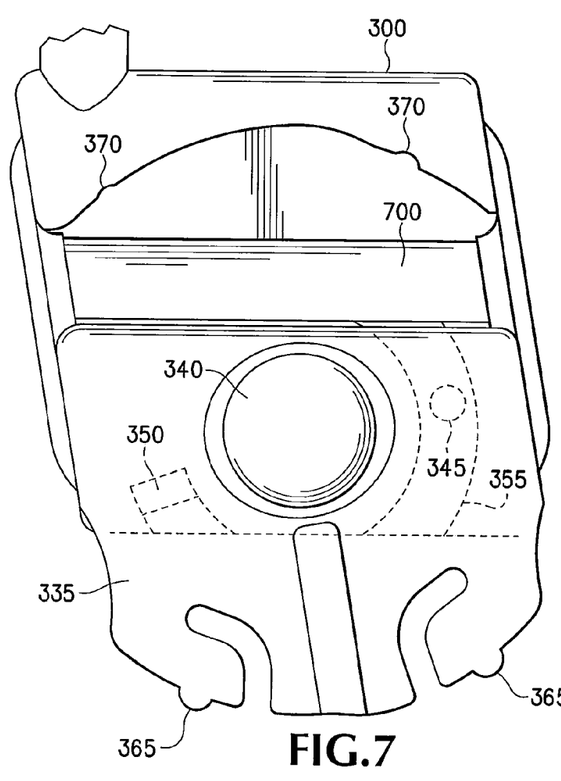
FIG. 7 is a top view of a self-ligating orthodontic bracket with a rotary ligating cover in an open position, exposing an archwire slot within a bracket base, according to one embodiment of the invention.

FIG. 7 is a top view of a self-ligating orthodontic bracket, according to one embodiment, as in FIG. 6A, except that the rotary ligating cover 335 is in an open position, exposing the archwire slot 700 formed upon the bracket base 315. Here, the rotary ligating cover 335 has been rotated in a counterclockwise direction until the archwire slot 700 is fully exposed. Through this portion of rotation, the rotation stop 345 has tracked within the circular recess 355. In one embodiment, the rotation stop 345 moves up against an end in the circular recess 355 (not shown) for stopping the counterclockwise rotation of the rotary ligating cover 335 when the archwire slot 700 becomes fully exposed.

Figure 8:
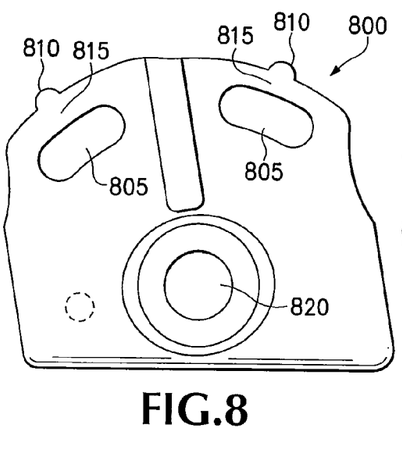
FIG. 8 is a top view of a rotary ligating cover according to an alternate embodiment of the invention.

As will be appreciated, variations of the self-ligating orthodontic bracket described herein may be apparent. For example, FIG. 8 illustrates a top view of a rotary ligating cover 800 according to an alternate embodiment of the invention. The rotary ligating cover 800 incorporates relief areas 805 cut out behind the locking tabs 810 leaving resilient retention features 815 that deflect inward, in directions coplanar with the rotary ligating cover and toward the axial member 820 about which the rotary ligating cover is able to pivot. For example, as the rotary ligating cover 800 rotates into a closed position, the resilient retention features 815 deflect inward in directions perpendicular with the pivot axis of the axial member 815, allowing the locking tabs 810 to engage with cooperatively mating cut out portions or indentations (not shown) in the bracket base.

Figure 9:
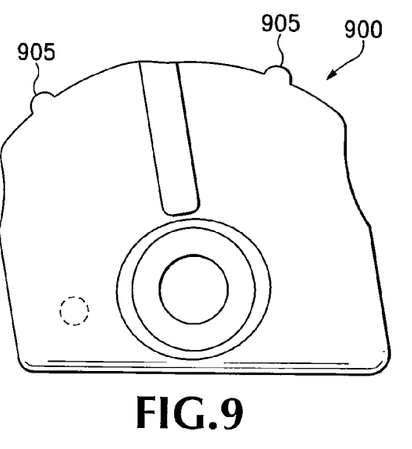
FIG. 9 is a top view of a rotary ligating cover according to another alternate embodiment of the invention.

FIG. 9 is a top view of a rotary ligating cover 900 according to another alternate embodiment of the invention. The rotary ligating cover 900 incorporates one or more locking tabs 905 which engage with cooperatively mating cutout portions or indentations (not shown) in the bracket base when the rotary ligating cover 900 is rotated into a closed position. The one or more locking tabs 905 are preferably aligned in coplanar relation to rotary ligating cover 900 as shown, cooperatively mate with cutout portions in the bracket base (not shown), and are capable of exerting retention forces in a direction coplanar with the rotary ligating cover and, thereby, holding the rotary ligating cover in a closed position.

Figure 10:
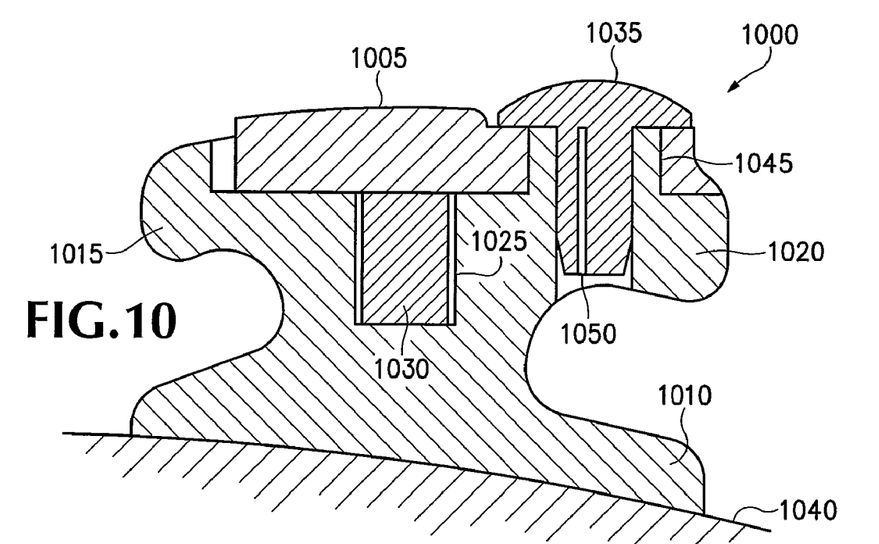
FIG. 10 is a sectional view of a self-ligating orthodontic bracket with a rotary ligating cover in a closed position, according to an alternate embodiment of the invention.

FIG. 10 is a sectional view of a self-ligating orthodontic bracket 1000 (along its centerline as in FIG. 4) with a rotary ligating cover 1005 in a closed position, according to an alternate embodiment of the invention. Similar with the bracket shown in FIG. 4, bracket 1000 comprises a mounting base 1010 for mounting the bracket 1000 upon a tooth surface 1040 and a pair of tie wings 1015 and 1020 formed upon the mounting base 1010, extending outward therefrom and defining an archwire slot 1025 therebetween. The rotary ligating cover 1005 is rotatably fastened upon one of the tie wings 1020 and is capable of rotatably and securely closing over the archwire slot 1025 and an archwire 1030 therein. However, the rotary ligating cover 1005 may be rotatably fastened using a retaining pin 1035 that fits into a bushing 1045 formed upon the tie wing 1020. The retaining pin 1035 may be any fastener with a pan head or similar head structure capable of retaining the rotary ligating cover 1005 by overlapping the outward surface of the bushing 1045 and a portion of the outward surface of the rotary ligating cover 1005 extending outward from the bushing 1045. In one embodiment, the retaining pin 1035 includes one or more axial ribs 1050 for improving interference fit and retention forces of the retaining pin 1035 within the bushing 1045 and hole or recess extending below the bushing 1045 toward the bracket mounting base 1010.

Figure 11:
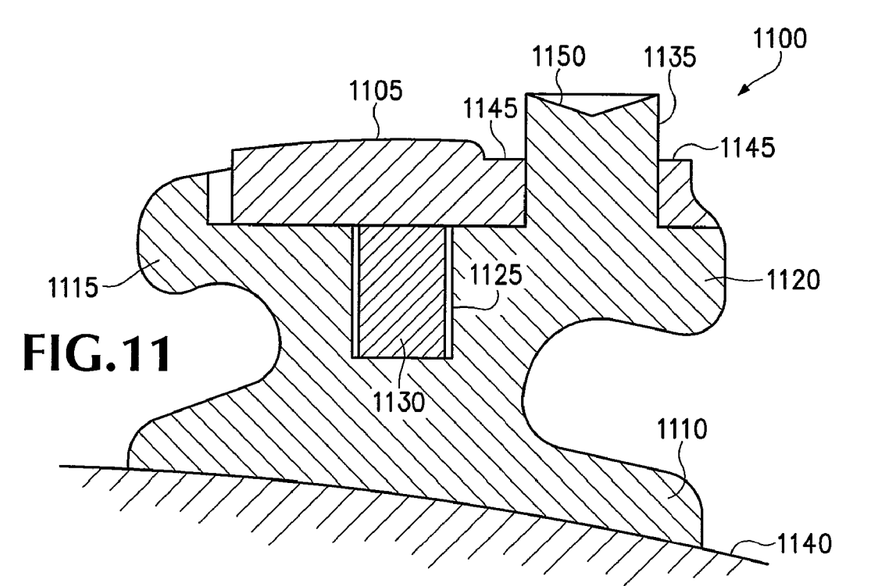
FIG. 11 is a sectional view of a self-ligating orthodontic bracket with a rotary ligating cover in a closed position, according to another alternate embodiment of the invention.

FIG. 11 is a sectional view of a self-ligating orthodontic bracket 1100 (along its centerline as in FIG. 4) with a rotary ligating cover 1105 in a closed position, according to another alternate embodiment of the invention. Similar with the bracket shown in FIG. 4, bracket 1100 comprises a mounting base 1110 for mounting the bracket 1100 upon a tooth surface 1140 and a pair of tie wings 1115 and 1120 formed upon the mounting base 1110, extending outward therefrom and defining an archwire slot 1125 therebetween. The rotary ligating cover 1105 is rotatably fastened upon one of the tie wings 1120 and is capable of rotatably and securely closing over the archwire slot 1125 and an archwire 1130 therein. However, the rotary ligating cover 1105 may be rotatably fastened about a stud 1135 formed upon the tie wing 1120 and coined (or mushroomed) to retain the rotary ligating cover 1105. FIG. 11 shows the sectional view prior to the coining operation. During the coining operation, some of the material comprising the stud 1135 is displaced inward, toward the bracket mounting base 1110, and radially outward from the stud 1135 to overlap an annular portion 1145 of the outward surface of the rotary ligating cover 1005 immediately adjacent to the stud 1135. To facilitate the coining operation and to improve the repeatability and consistency of the overlap of the annular portion 1145 of the rotary ligating cover 1105, a recess such as a conical recess 1150 may be formed upon the outward facing surface of the stud 1135 (as shown). Likewise, other scribe lines or recess areas may be included as may be needed depending upon the particular coining process and materials chosen for the bracket 1100.

Figure 12A:
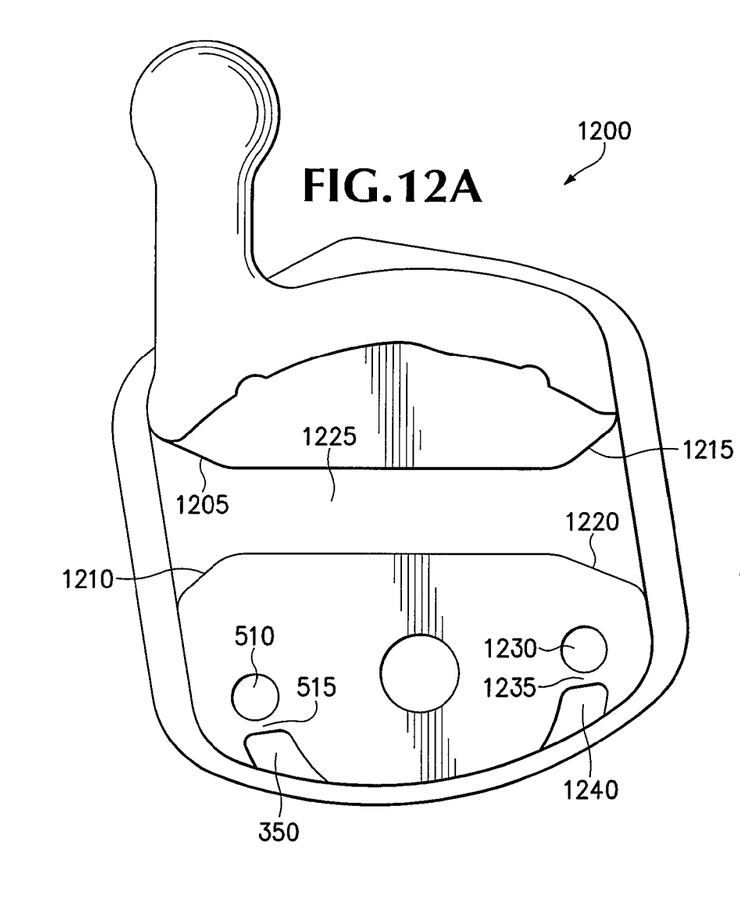
FIGS. 12A and 12B are top views of self-ligating orthodontic bracket bases each having lead in chamfers on the archwire slot, according to various embodiments of the invention.
Figure 12B:
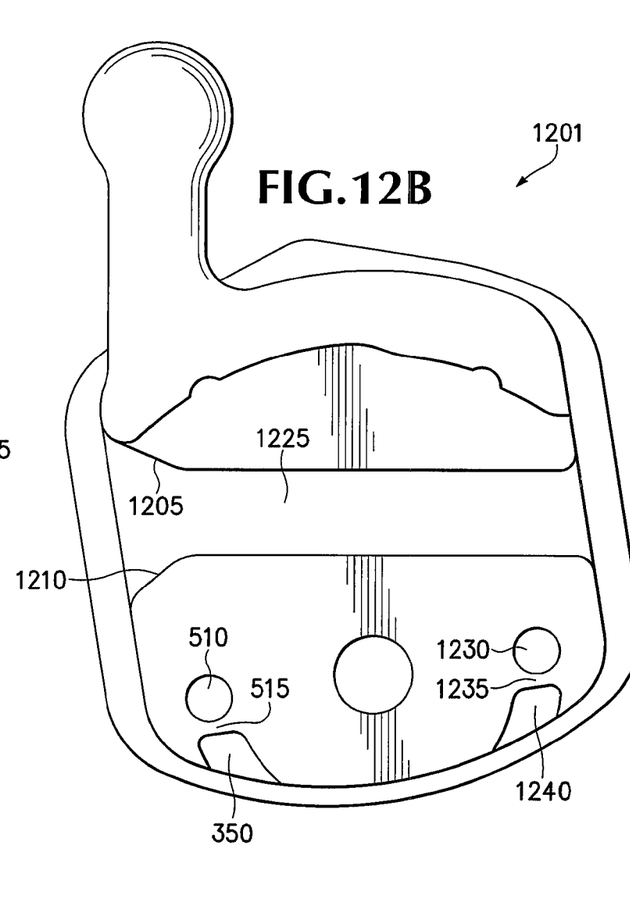

FIG. 12A is a top view of a self-ligating bracket base 1200 having lead in chamfers 1205, 1210, 1215, and 1220 on the archwire slot 1225, according to one embodiment of the invention. The lead in chamfers may be provided to improve the ease with which an archwire is inserted into and adjusted within the archwire slot 1225. Each lead in chamfer comprises an edge beveled to achieve a widened and tapered surface leading into the (narrower) archwire slot. The lead in chamfers may be on one or both ends of the archwire slot 1225. For example, as shown in FIG. 12B for bracket base 1201, the lead in chamfers 1205 and 1210 may be included on a distal end of an archwire slot 1225 having a mesial-distal axis. As shown in FIG. 12A, additional lead in chamfers 1215 and 1220 may be included on the other (for example, mesial) end of the archwire slot 1225. However, the archwire slot 1225 may incorporate any one or any combination of more than one (or none) of the lead in chamfers 1205, 1210, 1215, and 1220.

The archwire 1225 preferably includes chamfers on both ends, such as lead in chamfers 1205 and 1210 on one end and lead in chamfers 1215 and 1220 on the other. As shown, the lead in chamfer 1205 may be oriented on one gingival-occlusal opening edge of the archwire slot 1225, and the lead in chamfer 1210 may be oriented on the opposite gingival-occlusal opening edge. Likewise, the lead in chamfer 1215 may be oriented on one gingival-occlusal opening edge on the opposite end of the archwire slot 1225, and the lead in chamfer 1220 may be oriented on the opposite gingival-occusal opening edge. Although not shown in FIG. 12A, lead in chamfers on the labial-lingual opening edges of the archwire slot 1225 may be included.

Also shown in FIG. 12A are recessed areas within the self-ligating bracket base 1200 that are sized to receive a rotational stop or protruding nub formed upon the lower surface of the rotary ligating cover (not shown), according to one embodiment. As with other cooperatively mating features described herein, the locations of the one or more recessed areas and cooperatively mating one or more rotational stops may be reversed. For example, the rotational stop may be formed upon the bracket base 1200, and the recessed areas sized to receive the rotational stop may be formed upon the lower surface of the rotary ligating cover. For the benefit of concisely describing operation of various embodiments, the recessed areas are illustrated as being formed upon the outward surface of the bracket base 1200. The cross-sectional view in these areas of the bracket may be similar to the cross-sectional view shown in FIG. 5C. That is, the self-ligating bracket base 1200 may include a concentric circular recess 350 formed upon the outward surface of the bracket base within which a rotational stop formed upon the lower surface of the rotary ligating cover may track when the rotary ligating cover is rotated. In operation, as the rotary ligating cover is rotated (in a clockwise direction, for example) the rotational stop may enter the circular recess 350, ride over bracket material 515 at the end of the circular recess 350, and seat into a detent 510, thereby holding the rotary ligating cover in a particular position (either open, exposing the archwire slot 1225, or closed, covering the archwire slot 1225).

In one embodiment, the self-ligating bracket base 1200 includes a second concentric circular recess 1240 formed upon the bracket base within which the rotational stop may track when the rotary ligating cover is rotated. As the rotary ligating cover is rotated (in a counterclockwise direction, for example) the rotational stop may enter the circular recess 1240, ride over the bracket material 1235 at the end of the circular recess 1240, and seat into a detent 1230, thereby holding the rotary ligating cover in a particular (open or closed) position.

The location of the rotational stop formed upon the lower surface of the rotary ligating cover may be, according to one embodiment, oriented to determine the direction of rotation for exposing or covering the archwire slot 1225. All brackets in a particular prescription of brackets may, for example, be configured so as to open (to expose the archwire thereunder) using the same direction of rotation of the rotary ligating cover (such as counterclockwise). Or, some brackets may be configured to open with a counterclockwise rotation and others with a clockwise rotation. For example, if it is desired to mount the brackets on the teeth so that each bracket has its axis of rotation (such as the axis of rotation 250 shown in FIG. 2) positioned on the occlusal side of the archwire slot, and if it is desired to configure the brackets so that the archwire is exposed by applying pressure in the mesial direction (i.e. applying pressure directed toward the front teeth or centrals), each of the brackets may be configured to open in either a clockwise direction or a counterclockwise direction depending upon the bracket's intended location in the mouth. In this example, the orthodontist might open each bracket by placing an orthodontic tool on the distal edge of the bracket's rotary ligating cover and exerting pressure in the mesial direction. For the brackets mounted on teeth in the upper left or lower right (Palmer) quadrants, the rotary ligating cover for each bracket would be opened by rotating the cover in a counterclockwise direction. For the brackets mounted on teeth in the upper right or lower left quadrants, the rotary ligating cover for each bracket would be opened by rotating the cover in a clockwise direction.

Assuming, for example, that the bracket in FIG. 12A is configured so that the rotary ligating cover may be opened to expose the archwire slot 1225 by rotating the cover in a counterclockwise direction, the rotational stop formed upon the lower surface of the rotary ligating cover may be located so that it is seated within detent 510 when the rotary ligating cover is closed over the archwire slot 1225. When the rotary ligating cover is rotated counterclockwise, the rotational stop (such as rotational stop 345 in FIG. 5C) moves from its position seated within detent 510, rides over the bracket material 515 between the detent 515 and the end of the circular recess 350, and then tracks within the circular recess 350 until moving freely in space until entering the circular recess 1240 on the other side of the bracket base 1200. As the rotary ligating cover continues its counterclockwise rotation, the rotational stop rides over the bracket material 1235 and becomes seated within the detent 1230 beyond the end of the circular recess 1240. The detent 1230 may be located so as to hold the rotary ligating cover in an open position, fully exposing the archwire slot 1225.

Figure 13:
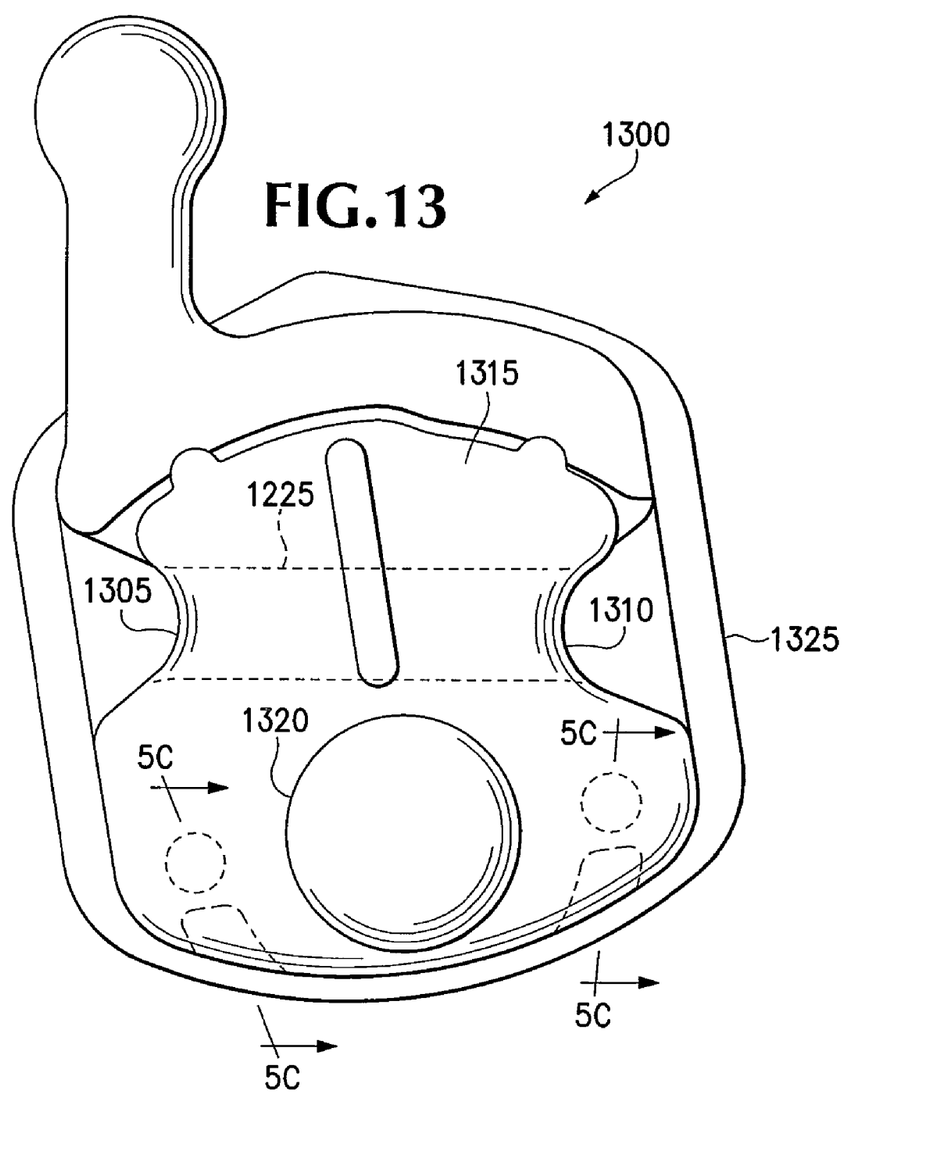
FIG. 13 is a top view of a self-ligating bracket with cutouts on the sides of a rotary cover, according to one embodiment of the invention.

FIG. 13 is a top view of a self-ligating bracket 1300 with cutouts 1305, 1310 on the sides of a rotary cover 1315, according to one embodiment of the invention. As shown, a pair of cutouts 1305, 1310 on said rotary ligating cover 1315, each one oriented transverse to said archwire slot 1225, is provided for manipulation of the rotary ligating cover 1315 to expose or cover the archwire slot 1225 thereunder. If, for example, the rotary ligating cover 1315 is to be opened to expose the archwire slot 1225 by rotating the cover 1315 in a counterclockwise direction about an axial member 1320, an orthodontic tool may be used to apply pressure on the cutout 1310 in a direction parallel to the archwire slot 1225 and toward the cutout 1305 at the opposite end of the archwire slot 1225. In similar fashion, for this example, the rotary ligating cover 1315 may be closed to cover the archwire slot 1225 by rotating the cover 1315 in a clockwise direction about the axial member 1320 using an orthodontic tool to apply pressure on the cutout 1305. As previously described, the directions of rotation for opening and closing the rotary ligating cover 1315 may be reversed.

The self-ligating orthodontic bracket described herein may comprise any of a wide variety of aesthetics suitable for use in an orthodontic appliance. For example, the brackets may comprise a prescription of brackets with each individual bracket having multiple colors, adjacent brackets having different colors, or groups of brackets having different colors. The brackets may be opaque or translucent or combinations thereof. For instance, the bracket base 1325 in FIG. 13 may be opaque (or a particular color), and the rotary ligating cover 1315 may be translucent. Or, as another example, the bracket 1300 may have its base 1325 and rotary ligating cover 1315 in one color and one of the cutouts, such as cutout 1310, marked with a different color as a visual aid to indicate which of the cutouts 1305, 1310 to use when opening the rotary ligating cover 1315 to expose the archwire slot 1225 thereunder. Or, as yet another example, the bracket base 205 in FIG. 2 may be the same color as the rotary ligating cover 210, and the retaining pin 215 may be a different color so as to aid in placement of the bracket 200 upon a tooth and subsequent manipulation of the rotary ligating cover 210. Numerous other variations involving the use of different colors are possible.

The self-ligating orthodontic bracket described herein may comprise any of a wide variety of materials suitable for use in an orthodontic appliance. Such materials have commonly included plastics, ceramics, stainless steel, titanium, or other metal alloys. The bracket preferably comprises a biocompatible material with corrosion resistive properties, and the bracket preferably comprises materials which may be formed into the structures shown yet maintain suitable strength characteristics for retaining commonly used orthodontic archwires or other components of an orthodontic appliance.

Nickel may be the most common metal associated with contact dermatitis in orthodontics. Recent figures suggest that perhaps 10% of patients are sensitive to nickel. Nevertheless, nickel-containing metal alloys, such as nickel-titanium and stainless steel, are widely used in orthodontic appliances. Nickel-titanium alloys may have nickel contents above 50% and may potentially release enough nickel in the oral environment to elicit manifestations of an allergic reaction. Stainless steel has a much lower nickel content, perhaps around 8%, and, because the nickel is bound in a crystal lattice within stainless steel, the nickel may be less available to react. Consequently, stainless steel orthodontic components may be less likely to cause nickel hypersensitivity.

However, because of the remaining uncertainty regarding a particular patient's sensitivity to nickel, it may be desirable to provide nickel-free orthodontic brackets to avoid nickel hypersensitivity altogether. Therefore, the self-ligating orthodontic bracket described herein preferably comprises a nickel-free material. In one embodiment, the bracket comprises a nickel-free cobalt-chromium alloy.

Several methods may be used to manufacture the self-ligating orthodontic bracket described herein. For example, the bracket may be cast, machined, injection molded and so on. Injection molding of plastics may be used as may be ceramic injection molding (CIM) or metal injection molding (MIM) depending upon the materials chosen. The bracket may comprise a molded base coupled with a molded rotary ligating cover that is coined to hold the cover to the bracket, or the bracket may comprise a molded base coupled with a molded ligating cover fastened to the bracket using a separate axial member press-fit onto the bracket. For instance, the bracket may comprise the assembly of a formed bracket body and a formed rotary ligating cover, the rotary ligating cover retained upon a tie wing of the bracket body following a coining operation whereby a stud protruding from the bracket body is mushroomed or coined to retain the rotary ligating cover thereon. A ball hook, or other components, may be welded to the bracket assembly or formed as part of the bracket body (i.e., as part of the molded bracket body).

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. A self-ligating bracket having:
   a mounting base for attachment to a tooth surface;
   an archwire slot formed upon said base and sized for receiving an orthodontic archwire;
   a rotary ligating cover selectively rotatable between an open position permitting access to said archwire slot and a closed position covering said archwire slot, said rotary ligating cover comprising a plate eccentrically rotatably mounted on an axial member journalled into said base;
   a pair of cutouts on said rotary ligating cover oriented transverse to said archwire slot for manipulation of said rotary ligating cover to expose or cover said archwire slot thereunder;
   one or more locking features adjacent said archwire slot for holding said rotary ligating cover in a closed position, wherein said one or more locking features comprise one or more locking tabs formed upon one of said rotary ligating cover and said base, said one or more locking tabs aligned in coplanar relation to said rotary ligating cover and cooperatively mating with cutout portions in the other of said rotary ligating cover and said base;
   one or more concentric circular recesses formed upon either said lower surface of said plate or said outward surface of said base within which a rotational stop formed upon the other of said lower surface of said plate or said outward surface of said base track when said plate is rotated, said one or more concentric circular recesses and said rotational stop, in combination, defining an opening direction and a closing direction of said plate; and
   one or more detents associated with each of said one or more concentric circular recesses and configured to receive said rotational stop thereby holding said plate in an open or closed position.

2. The bracket of claim 1, further comprising a pair of tie wings extending from said base and defining said archwire slot between said tie wings.

3. The bracket of claim 1, further comprising at least one resilient retention mechanism adjacent to said one or more locking tabs and aligned in coplanar relation to said rotary ligating cover, said at least one resilient retention mechanism capable of exerting retention forces in a direction coplanar with said rotary ligating cover.

4. The bracket of claim 3, wherein said at least one resilient retention mechanism includes one or more relief channels permitting flexing of at least portions of said resilient retention mechanism adjacent to said one or more locking tabs.

5. The bracket of claim 1, further comprising a pair of tie wings extending from said base and defining said archwire slot between said tie wings, said axial member journalled into a first one of said tie wings, said plate rotatably closable over said archwire slot and cooperatively mating with outward surfaces in a second one of said tie wings.

6. The bracket of claim 1, wherein said axial member comprises a retaining pin for rotatably fastening said plate to a hole in said base sized for receiving said retaining pin.

7. The bracket of claim 1, wherein said axial member comprises a retaining pin for rotatably fastening said plate to a hole within a bushing formed upon said base, said hole sized for receiving said retaining pin.

8. The bracket of claim 1, wherein said axial member comprises a stud formed upon said base and coined to rotatably fasten said plate to said base.

9. The bracket of claim 1, further comprising lead in chamfers on one or both ends of said archwire slot.

10. A self-ligating orthodontic bracket having:
   a mounting base for attachment to a tooth surface;
   an archwire slot formed upon said base and sized for receiving an orthodontic archwire;
   lead in chamfers on one or both ends of said archwire slot;
   a rotary ligating cover selectively rotatable between an open position permitting access to said archwire slot and a closed position covering said archwire slot, said rotary ligating cover comprising a plate eccentrically rotatably mounted on an axial member journalled into said base and a pair of cutouts on said plate oriented transverse to said archwire slot for manipulation of said rotary ligating cover to expose or cover said archwire slot thereunder;
   one or more locking features adjacent said archwire slot for holding said rotary liqatinq cover in a closed position, wherein said one or more locking features comprise one or more locking tabs formed upon one of said rotary ligating cover and said base, said one or more locking tabs aligned in coplanar relation to said rotary ligating cover and cooperatively mating with cutout portions in the other of said rotary ligating cover and said base;
   one or more concentric circular recesses formed upon either said lower surface of said plate or said outward surface of said base within which a rotational stop formed upon the other of said lower surface of said plate or said outward surface of said base track when said plate is rotated, said one or more concentric circular recesses and said rotational stop, in combination, defining an opening direction and a closing direction of said plate; and
   one or more detents associated with each of said one or more concentric circular recesses and configured to receive said rotational stop thereby holding said plate in an open or closed position.

11. The bracket of claim 10, further comprising a pair of tie wings extending from said base and defining said archwire slot between said tie wings.

12. The bracket of claim 10, further comprising at least one resilient retention mechanism adjacent to said one or more locking tabs and aligned in coplanar relation to said rotary ligating cover, said at least one resilient retention mechanism capable of exerting retention forces in a direction coplanar with said rotary ligating cover.

13. The bracket of claim 12, wherein said at least one resilient retention mechanism includes one or more relief channels permitting flexing of at least portions of said resilient retention mechanism adjacent to said one or more locking tabs.

14. The bracket of claim 10, further comprising a pair of tie wings extending from said base and defining said archwire slot between said tie wings, said axial member journalled into a first one of said tie wings, said plate rotatably closable over said archwire slot and cooperatively mating with outward surfaces in a second one of said tie wings.

15. The bracket of claim 10, wherein said axial member comprises a retaining pin for rotatably fastening said plate to a hole in said base sized for receiving said retaining pin.

16. The bracket of claim 10, wherein said axial member comprises a retaining pin for rotatably fastening said plate to a hole within a bushing formed upon said base, said hole sized for receiving said retaining pin.

17. The bracket of claim 10, wherein said axial member comprises a stud formed upon said base and coined to rotatably fasten said plate to said base.

* * * * *